United States Patent [19]

Leedham et al.

[11] Patent Number: 4,652,451

[45] Date of Patent: Mar. 24, 1987

[54] CONTROLLING ALCOHOL FERMENTATIONS

[75] Inventors: Peter A. Leedham, North Crawley; Roy S. Tubb, Burstow, Nr. Horley, both of England

[73] Assignee: Whitbread & Co., Ltd., London, England

[21] Appl. No.: 475,655

[22] Filed: Mar. 15, 1983

[30] Foreign Application Priority Data

Mar. 15, 1982 [GB] United Kingdom ................. 8207515

[51] Int. Cl.$^4$ ............................................. C12C 11/00
[52] U.S. Cl. ........................................ 426/11; 426/16; 435/161; 435/313
[58] Field of Search .................. 426/11; 435/161, 313, 435/162

[56] References Cited

U.S. PATENT DOCUMENTS 4,346,113  8/1982  Faust et al. ......................... 435/161

OTHER PUBLICATIONS

Rose–Economic Microbiology, vol. Alcoholic Beverages (1977) Acad. Press, pp. 551 & 552.

*Primary Examiner*—Sam Rosen
*Attorney, Agent, or Firm*—Sughrue, Mion, Zinn, Macpeak, and Seas

[57] ABSTRACT

In the initial stages of a fermentation of carbohydrate to form alcohol, the growth of the yeast is controlled by monitoring the pH value of a fermenting liquid or wort and controlling the supply of oxygen to the fermenting liquid or wort in accordance with the pH value. Preferably the temperature of the fermenting liquid is also controlled in dependence upon the pH value of the fermenting liquid or wort. It is particularly preferred that the control of the fermentation process is carried out automatically by an apparatus including a fermentation vessel 1, a pH sensor 8, 9, 10 arranged to provide an output signal representative of the pH of the liquid in the vessel 1, memory means to store information on the required pH with regard to the fermentation time, means 11, 12, 13 to inject oxygen into the fermenting liquid and control means 15 to compare the output signal of the pH sensor at a particular time with that of the required pH at that time, and, in the event of the pH of the fermenting liquid lagging behind that required, actuate the means 11, 12, 13 to inject oxygen into the fermenting liquid to increase the oxygen content of the fermenting liquid.

7 Claims, 2 Drawing Figures

CONTROLLING ALCOHOL FERMENTATIONS

This invention relates to the control of carbohydrate fermentations to produce alcohol. In batch fermentation of carbohydrates to produce alcohol there is an initial period which typically lasts between 24 and 48 hours, during which yeast introduced reproduces and multiplies. Sufficient yeast has to be grown during this initial period to ensure that the subsequent fermentation proceeds at a sufficiently fast rate. However, it is desirable that not too much yeast is grown so wasting carbohydrate by producing too much yeast instead of using it to produce alcohol which is the desired end product. After the initial period, substantially no more yeast is grown and instead, the fermentation proceeds with the carbohydrate being converted to alcohol.

There is a need to control the fermentation of carbohydrate in the production of alcohol because if the fermentation times are irregular, this leads to difficulties. Further, when the carbohydrate is fermented to produce a potable liquid, variations in the fermentation lead to variations in the flavour and taste of the resulting potable liquid which is again undesirable. At present, most fermentations are controlled either manually or semi-automatically but this control is not inter-active in that the control does not respond to correct irregularities or respond to changes in the fermentation. The control is exercised by operating to a preset programme to control temperature and any additions to the fermentation. Naturally, some additional manual adjustments have to be made when it appears that a fermentation is not proceeding in the required way. At present, the carbohydrate and alcohol concentrations are measured during various stages of the fermentation and it is these which are monitored to determine whether the fermentation is proceeding in the required way. As a result of the monitored concentrations of alcohol and carbohydrate indicating that the fermentation is proceeding irregularly, a manual adjustment is made to the fermentation but we have found that these manual adjustments are usually made too late to be fully effective in correcting the irregularities.

We have found that the growth of yeast during the initial period of the fermentation is critical if regular fermentations are to be obtained. If the quantity of yeast grown during the initial period is controlled correctly then it is relatively straightforward to ensure that the remainder of the fermentation is carried out in a consistent and reproducible fashion. The traditional measurements of the concentrations of carbohydrate and alcohol change only very slightly during this initial period of the fermentation since, in this period, very little of the carbohydrate is converted into alcohol. Thus, it is very difficult to detect any change in the concentrations of the carbohydrate and alcohol during this initial period and consequently, with the traditional measurements that are carried out, it is difficult to exercise any effective control on the quantity of yeast produced during this initial period.

There is a significant change in the pH value of the fermenting liquid or wort during the initial fermentation period and we have found that this change in the pH of the fermenting liquid or wort shows a close correlation to the growth of the yeast.

According to this invention we make use of this knowledge by monitoring the pH value of a fermenting liquid or wort and controlling the supply of oxygen to the fermenting liquid or wort in accordance with the pH value and so control the growth of the yeast during the initial stages of fermentation.

Preferably the temperature of the fermenting liquid is also controlled in dependence upon the pH value of the fermenting liquid or wort. The value of the pH of the fermenting liquid may also be used to control the addition of various essential vitamins and minerals that are required to enable the yeast to grow but, in general, these materials are usually present as part of the raw materials and are extracted into the wort during the mashing process.

The quantity of yeast that is grown in the initial period of a fermentation is limited by the availability of oxygen in the fermenting liquid whereas the temperature of the fermenting liquid controls the rate of growth of the yeast. In practice, fermentations start with an oxygen deficiency. Brewery wort is prepared by boiling water together with the various raw materials and this boiling step removes the oxygen initially dissolved in the water. Equally, the preparation of a wash which is to be fermented and then subsequently distilled to produce industrial alcohol or an alcoholic spirit usually includes a boiling step in which water and the various raw materials are boiled together. Thus, the liquid to be fermented usually starts with an oxygen deficiency and thus by controlling the addition of oxygen to, and if necessary the temperature of, the fermenting liquid, the quantity and the rate of growth of the yeast in the initial fermentation period can be controlled with great precision.

Preferably the pH of the fermenting liquid is monitored during the initial stages of the fermentation and compared with a predetermined programme for the required pH of the fermenting liquid during the initial stages of its fermentation. Naturally, this predetermined programme for the pH varies with the initial pH of the boiled wort or wash and the intended product. Thus, a wort for producing lager has a different pH programme from one for ale and equally, both of these have a different pH programme from that for a wash which is to be fermented and subsequently distilled to produce industrial alcohol or an alcoholic spirit.

It is only during the initial period of fermentation that the fermentation need be controlled by monitoring its pH and, after this initial period, typically after the first 24 to 48 hours, the fermentation is then controlled by monitoring the percentage alcohol and carbohydrate present in the fermenting liquid in a conventional manner.

This method may be carried out manually but, in view of the large number of personnel that would be required to monitor the number of fermentations which are typically carried out simultaneously in a modern brewery it is particularly preferred that the control of the fermentation process is carried out automatically by an apparatus including a fermentation vessel, a pH sensor arranged to provide an output signal representative of the pH of a fermenting liquid in the vessel, memory means to store information on the required pH with regard to the fermentation time, means to inject oxygen into the fermenting liquid in the vessel, control means to compare the output signal of the pH sensor at a particular time with that of the required pH at that time, and, in the event of the pH of the fermenting liquid lagging behind that required, actuate the means to inject oxygen into the fermenting liquid to increase the oxygen content of the fermenting liquid.

The apparatus may also include temperature control means to increase the temperature of the fermenting liquid and in this case, the control means may additionally actuate the temperature control means in the event of the pH of the fermenting liquid lagging behind that required.

The temperature control means may be a heater in the vessel to heat the fermenting liquid in the vessel but, usually, since the fermentation is exothermic, the fermentation vessel normally includes a cooling jacket through which a cooling fluid passes to maintain the fermenting liquid at a particular temperature. In this case the temperature control means controls the flow of cooling fluid through the cooling jacket to allow the fermenting liquid to heat itself up by the exothermic fermentation taking place within it.

Preferably the apparatus includes means to monitor the temperature of the fermenting liquid in the vessel, and the memory means also stores information on the required temperature at which the fermentation is to be carried out. In this case, the control means also compares the output from the temperature sensor with the information on the required temperature at which the fermentation is to be carried out. The control means normally actuates the temperature control means to maintain the temperature of the fermenting liquid at the required temperature but, in the event of the pH sensor detecting a lag in the growth of the yeast the control means actuates the temperature control means to increase the temperature of the fermenting liquid above the required temperature to boost the rate of growth of the yeast.

The apparatus is preferably arranged to monitor the pH and the temperature of the fermenting liquid at predetermined intervals. The predetermined intervals may typically be every 15 minutes.

Preferably the control means is formed by a programmed computer and in this case the computer is programmed to monitor the pH of the fermentation at the predetermined intervals, compare the monitored pH with the required pH and actuate the means to inject oxygen into the fermentation vessel in the event of the pH of the fermenting liquid lagging behind the required pH of the liquid at that point. The programmed computer is preferably also arranged to monitor the temperature of the fermenting liquid, compare the monitored temperature with the temperature required at that time and control the temperature control means to maintain the temperature of the fermenting liquid required at that time.

The memory means to store information may be formed by a separate information storage medium such as a magnetic tape or disc. The memory means may store data corresponding to the required pH and temperature of every type of fermentation at each predetermined interval. In this case, for each type of fermentation it is necessary to have several sets of information for each predetermined interval corresponding to the required pH at each stage, for a different initial pH of the liquid to be fermented. However, it is preferred that the computer is programmed to calculate the information with regard to the required pH at each predetermined interval from the initial pH of the liquid to be fermented and from the type of fermentation to be carried out which determines the fermentation time and the required pH at the end of the initial fermentation period. The required pH at each of the predetermined intervals for that particular fermentation is then recorded in a memory portion of the computer which, in this case, forms the memory means and is used as the required pH and temperature information for that fermentation. In this case, the apparatus preferably includes means to store information on the required fermentation time, the required final pH, the function which is used to determine the required pH at the predetermined intervals for the particular type of fermentation to be carried out, and the temperature required at each predetermined interval for that type of fermentation.

The apparatus is preferably arranged to monitor a number of different fermentations simultaneously and in this case, the apparatus includes a number of fermentation vessels, each of which includes one pH sensor and one temperature sensor to monitor the pH and the temperature of the fermenting liquid in that vessel, means to inject oxygen into the fermenting liquid in that vessel, and temperature control means to control the temperature of the fermenting liquid in that vessel, and the control means is arranged to select the sensors and means associated with that one particular fermentation vessel to monitor and control that one particular fermentation at a particular time. With the apparatus arranged in this way, the majority of the apparatus and particularly the most expensive parts of the apparatus is common for all of the fermentation vessels. The apparatus may be arranged to control more than one type of fermentation and, for example, when the apparatus is installed in a brewery, the apparatus may be arranged to control the fermentation of wort to produce ale, barley wine or lager. Each of these fermentations have a different desired pH at the end of the initial period of fermentation and a different required initial fermentation period. The different beers also have a different temperature programme which it is preferred that the temperature of the fermentation follows.

Preferably the temperature of the or each fermenting liquid is monitored and controlled substantially continuously by comparing the instantaneous output from the or each temperature sensor against the required temperature for that fermentation. This required temperature is set or reset by the computer at each predetermined interval.

Preferably the apparatus is arranged so that in the event of a lag in the monitored pH when compared with that required at one predetermined interval the control means first of all injects one unit of oxygen into the fermenting liquid. If at the next predetermined interval the pH still lags behind that required at that next interval, two units of oxygen are injected into the fermenting liquid. For the following three predetermined intervals if the pH lags behind that required, three units of oxygen are introduced at each interval. Following this sequence at the next predetermined interval, if the pH is still lagging behind that required, the required temperature of the fermenting liquid is increased by $\frac{1}{4}°$ C. For each of the following five intervals if the pH still lags behind that required then the required temperature of the fermenting liquid is raised by a further $\frac{1}{4}°$ C. However, at the last of these an alarm is also triggered to indicate that the control attempts are not succeeding. Naturally, during this sequence if at any predetermined interval the pH is in step with or in front of that required for that step, no further oxygen is supplied and if the required temperature of the fermenting liquid has already been increased then the required temperature is reduced to the normally required temperature for that time interval. Once the fermentation has been brought under control by the pH being in step with or in front of the required value the sequence of operations starts at the beginning again so that, in the event of a subsequent lag of pH behind that required at that predetermined interval the control that is exercised is the introduction of one unit of oxygen. Preferably each unit of oxygen is arranged to increase the oxygen content of the fermenting liquid by 0.1 parts per million.

Preferably the output from the pH sensor and temperature sensor associated with each fermentation vessel is recorded at each predetermined interval. This data may be recorded initially in the memory of the computer but, in any event, it is preferred that it is recorded on a permanent data recording medium such as a magnetic tape cassette or floppy disc, so that a complete record of each and every fermentation is contained on the permanent data storage medium. In this way, any subsequently detected fault in a particular fermentation can be compared with the permanent record of its initial fermentation period thereby to locate the cause of any fault in a fermentation and to enable preventative measures to be taken to ensure that the same fault does not occur on a future occasion.

A particular example of a method and apparatus in accordance with this invention which is arranged to control the fermentation of worts in a brewery will now be described with reference to the accompanying drawings in which.

Figure 1:
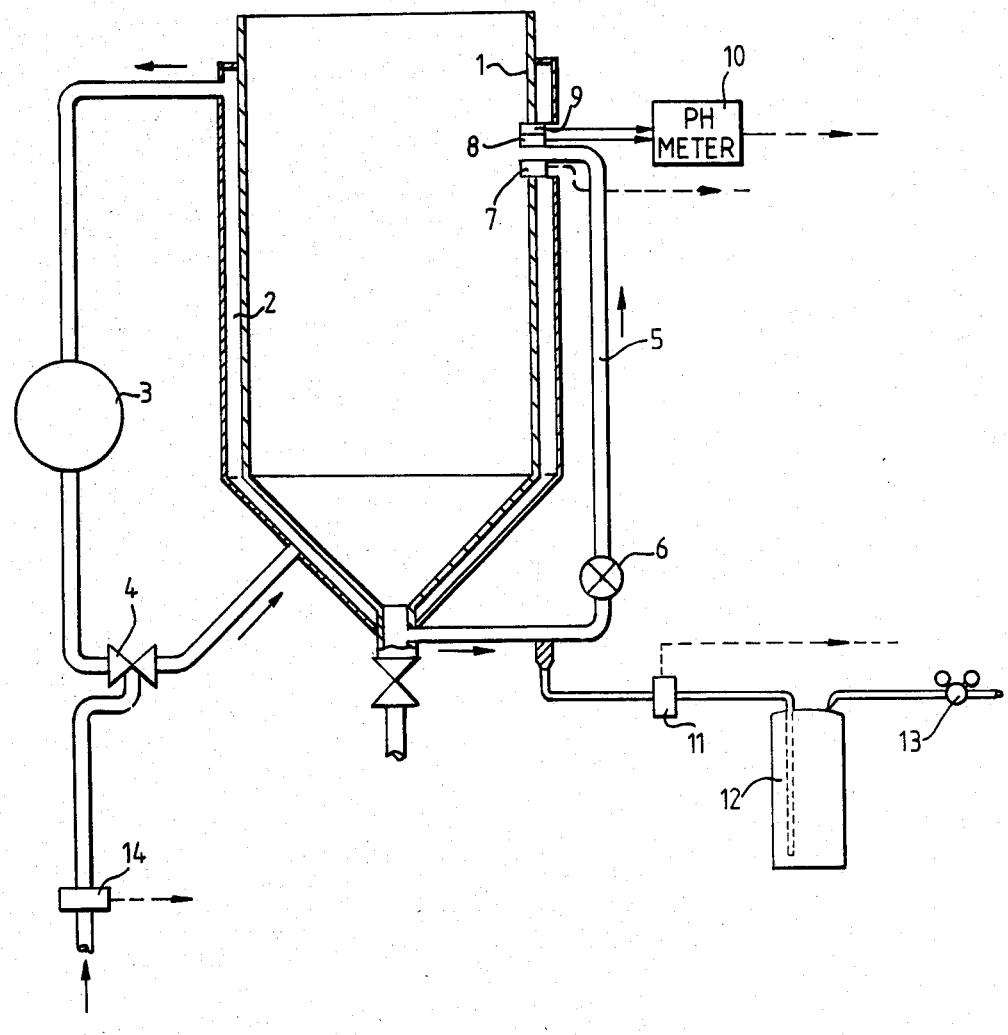
FIG. 1 is a diagram of the apparatus.

The apparatus comprises a fermentation vessel 1 including a cooling jacket 2 connected to a cooling system including a cooler 3 and a pneumatically operated coolant flow control valve 4. The fermentation vessel 1 also includes a sampling and recirculating loop 5 including a pump 6 by which the fermenting liquid is recirculated to ensure thorough mixing during the fermentation process. The fermentation vessel 1 also includes a platinum resistance thermometer 7 with its output connected to a 4–20 mA loop and acting as a temperature sensor, a pH electrode 8 and associated temperature compensator 9. The pH electrode 8 and temperature compensator 9 are, in this example, connected to a pH meter 10, although they may be directly connected to the control means to be described subsequently. The pH meter 10 is typically a Corning Model 125 with Model 47605000 combination pH electrode 8 and the temperature compensator 9 is typically model 47609500 automatic temperature compensator, both available from Paterson Scientific Limited, Harrow, United Kingdom.

The apparatus also includes an oxygenation system connected to the sampling and recirculation loop 5 via a solenoid controlled valve 11. The oxygenation system comprises a chilled, high pressure water reservoir 12 through which oxygen is supplied via control unit 13. The complete oxygenation system is manufactured by Caird and Rayner Limited of Watford, United Kingdom. A further solenoid controlled valve 14 controls the pneumatic supply to the pneumatically operated coolant flow control valve 4 and both solenoid controlled valves 11 and 14 are typically Pye Model CN224/TS 30137 valves obtainable from G. A. Platon Limited, Basingstoke, United Kingdom.

Figure 2:
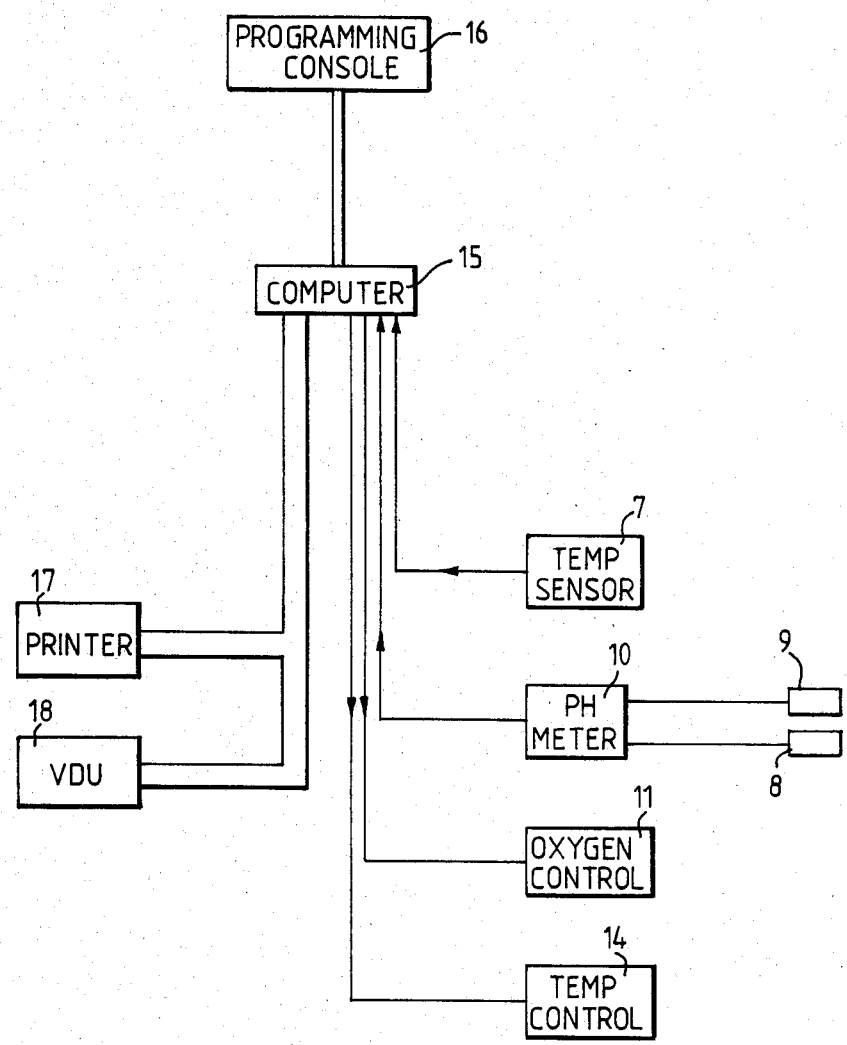
FIG. 2 is a block diagram of the control means.

The solenoid controlled valves 11 and 14, the thermometer 7, and the meter 10 are all connected to a central control means shown more clearly in FIG. 2 and comprising a computer 15 such as a 2 Kbit programmable logic controller, catalogue number PB 1902 fitted with analogue inputs, catalogue number PB1301; a DC output, catalogue number PB1251; and, an asynchronous coupler, catalogue number PV1075, all manufactured by Merlin Gerin Ltd, of Telford, United Kingdom. The control system also comprises a programming console 16, catalogue number OB2602; a printer 17, catalogue number PT1; and, a video display unit 18, again all available from Merlin Gerin Ltd. The computer 15 is programmed with a program based on the outline program listed below:

| I | Program starts | |
|---|---|---|
| II | pH of vessel scanned every 15 minutes | if outside set limits (i.e. vessel is empty) take no further action<br>if pH within starting limits for first time - go to step III<br>if fermentation has already started - go to step IV |
| III | Computer requests beer type code and in response to this being entered calculates the required pH, and establishes the required temperature set points and total initial fermentation time information for that fermentation. Also establishes and introduces preset quantity of oxygenated water for that fermentation. | |
| IV | Monitored pH compared with required pH | if high go to step VI<br>if at or below required value, go to step V |
| V | Record data | go back to II |
| VI | Introduce oxygenated water for x seconds | on first occasion x = 1<br>on second occasion x = 2<br>on third occasion x = 3<br>on fourth occasion x = 3<br>on fifth occasion x = 3<br>after fifth occasion go instead to step VIII |
| VIII | Increase required temperature set point by 1° C. per hour after the fifth increase in oxygen | if temperature is 3° C. above that required go to step X |
| IX | Record Data | go back to II |
| X | Sound Alarm | record data<br>go back to II |

At all times the computer controls the temperature of the fermenting liquid to within ±0.25° C. of the required temperature set point.

In use of this apparatus the boiled wort to be fermented is introduced into the fermentation vessel 1. The computer 15 monitors the temperature and pH values output by the thermometer 7 and the pH meter 10 respectively and, upon receiving a first reading of the pH corresponding to the first monitoring period after the wort to be fermented is introduced into the vessel 1 the computer requests the beer type code. This is keyed in via the programming console 16 and the beer type code corresponds to the conditions for an ale, barley wine or lager. Table I shows the temperature, pH and time conditions for the fermentation of these three different types of beer and all this information is stored in the internal memory of the computer 15. Upon the beer type code being inserted via the programming console 16 of the appropriate figures are withdrawn from the internal memory and incorporated in the program in the computer 15. Thus registers of the computer 15 are loaded with the information with regard to the required temperature set point for each of the monitoring steps, the final pH required and a counter is set with a number corresponding to the total number of monitoring steps involved in the initial fermentation period of that fermentation.

TABLE I

|  | ALE | BARLEY WINE | LAGER |
|---|---|---|---|
| Required temperature set point at start of fermentation (°C.) | 17 | 20 | 9 |
| Time (hours for which starting temperature is maintained) | 18 | 24 | 36 |
| Maximum allowable temperature (°C.) during starting stage | 20 | 23 | 12 |
| Required temperature set point afterwards (°C.) | 21 | 25 | 12 |
| Maximum allowable temperature (°C.) afterwards | 24 | 29 | 16 |
| Length of initial oxygenation/pH control period (hours) | 24 | 36 | 48 |
| Final pH required at end of initial oxygenation/pH control period | 4.00 | 4.10 | 4.20 |

The pH of the fermenting liquid is required to follow a third degree curve with one end of the curve being the starting pH of the liquid to be fermented and with the end of the curve being the final required pH. The computer 15 calculates the required pH at each monitoring period and stores these required pH figures in its internal memory registers. The boiled wort introduced into the fermentation vessel 1 has an oxygen deficiency as a result of it being boiled and the internal memory of the computer 15 also stores information about the initial quantity of oxygenated water that is to be introduced into the fermentation vessel 1. At the initial stage when the computer 15 is calculating the required pH values and loading these and the required temperature values into its internal memory registers, it also actuates the solenoid 11 to introduce this initial quantity of oxygenated water into the fermentation vessel 1. The liquid in the fermentation vessel 1 is pitched with yeast and, from then on, the fermentation is controlled by the computer 15.

The computer 15 operates substantially continuously a separate conventional temperature control program in which the output of the thermometer 7 is compared with the required temperature set point established by the main program and controls the solenoid controlled value 14 to control, in turn, the coolant flow control valve 4 to maintain the fermenting liquid at the required temperature.

At the next monitoring period, the computer 15 monitors the output of the pH meter 10 and compares this with the required values loaded in the registers of the memory. If the pH is at, or below, the required level the pH and temperature level sensed by the meter 10 and the thermometer 7 is recorded in the internal memory of the computer 15. If the monitored pH is above the required value, one unit of oxygen is introduced into the fermentation vessel through the solenoid control valve 11. The one unit of oxygen is arranged to increase the oxygen content of the fermenting liquid by 0.1 p.p.m. The temperature and pH of the fermenting liquid are recorded in the memory of the computer 15.

If at the next monitoring step the pH is still above that required, then two units of oxygen are introduced and again the temperature and pH data are recorded in the data store 18. At the next monitoring step if the pH is still above that required, then three units of oxygen are introduced and again the pH and temperature data are stored in the data store 18. This introduction of three units of oxygen is repeated for each of the next two successive monitoring steps if the monitored pH value is still above the pH value required for those steps.

After the fifth monitoring step in succession at which the pH is still above the required value the required temperature set point is increased by 0.25° C. to allow the fermenting liquid to heat up and so increase the rate of the yeast production. Again, the monitored pH and temperature values are recorded. The required temperature set point of the fermenting liquid is increased at each of the next six monitoring steps if the monitored pH is still above that required, and on the sixth such step an alarm is also sounded to indicate that the fermentation is not proceeding in accordance with the required regime and that the attempts to control the fermentation have not been successful. The temperature and pH of the fermenting liquid are recorded for each of these monitoring steps.

The computer 15 is arranged so that if the pH reaches or falls below the required value at any monitoring step after the commencement of the control sequence no control action is taken and the control sequence is reset so that, upon any subsequent actuation of the control sequence it begins by first adding one unit of oxygen to the fermenting liquid.

At the end of the initial period of the fermentation the stored values of the pH and temperature at each of the monitoring steps are transferred from the internal memory of the computer 15 onto, for example, a magnetic tape cassette so that they can be stored permanently. The programming console 16 includes a tape cassette read/write unit and this is used to load the initial program and information data into the computer 15. During the fermentation the data from the fermentation may be displayed on the printer 17 or visual display unit 18 via the asynchronous coupler.

The initial oxygenation of the liquid to be fermented that is carried out by the computer is deliberately arranged to under-oxygenate the liquid to be fermented at the start of the fermentation and thus, at the start of the fermentation the yeast is normally held in a position of slight insufficiency of oxygen. Therefore, it is anticipated that in every fermentation the control system is necessary to provide sufficient oxygen to enable a sufficient growth of yeast. Thus it is anticipated that the growth of the yeast in each and every fermentation is actively controlled by the operation of the system described. The computer 15 is arranged to increase the fermentation temperature towards the end of the initial period of fermentation as shown in Table I to accelerate the fermentation and reduce lagering or maturation periods for the resulting beer. Naturally, this programmed temperature change is overridden by the computer in the event of the monitored pH value lagging behind that required as already explained but apart from these special circumstances, the temperature of the fermentation follows the regime outlined in Table I.

Typically, a brewery contains a number of fermentation vessels 1, each with their own cooling jackets 2, coolant flow control valves 4 and associated solenoid controlled pneumatic valves 14, thermometers 7, pH electrodes 8 and temperature compensators 9, and solenoid controlled oxygenated water inlet 11. Each vessel 1 may include its own pH meter 10 but it is preferred in this case that the computer 15 calculates the pH from the outputs of the pH electrodes 8 and temperature compensators 9. These are all controlled by the same computer and associated elements shown in FIG. 2. In this case the computer 15 is arranged to monitor the thermometer 7, pH electrode 8 and temperature compensator 9 associated with each fermentation vessel 1 in succession and compare the monitored pH and temperature with the required values for that particular fermentation and carry out any control function that is required.

We claim:

1. A method of controlling a carbohydrate fermentation to produce alcohol comprising providing a fermenting liquid, monitoring the pH value of said fermenting liquid, and controlling supply of oxygen to said fermenting liquid in accordance with said monitored pH value and in the event the pH of said fermenting liquid lags behind the pH required for said fermentation, injecting oxygen into said fermenting liquid to increase the oxygen content of said fermenting liquid, whereby growth of yeast in said fermenting liquid during initial stages of said fermentation is controlled.

2. The method according to claim 1, wherein temperature of said fermenting liquid is also controlled in dependence upon said monitored pH value of said fermenting liquid.

3. The method according to claim 1 wherein said pH value of said fermenting liquid is monitored at predetermined intervals and said monitored pH is compared with pH values required at said predetermined intervals.

4. The method according to claim 3, wherein the pH value of liquid to be fermented is monitored and used to calculate said pH values required at said predetermined intervals in conjunction with information on the intended product of said fermentation.

5. The method according to claim 1, wherein the method is a batch method.

6. The method according to claim 5, wherein said method includes monitoring said pH value, comparing said pH value so monitored with a predetermined varying pH profile for the carbohydrate fermentation desired and varying the supply of oxygen to said fermenting liquid so that the pH of the fermenting liquid conforms to the predetermined pH profile for the carbohydrate fermentation desired.

7. The method according to claim 6, wherein said method includes controlling the temperature of said fermenting liquid in dependency upon said monitored pH value of said fermenting liquid.

* * * * *